United States Patent [19]
Tamai et al.

[11] Patent Number: 5,260,388
[45] Date of Patent: Nov. 9, 1993

[54] POLYIMIDE AND PROCESS FOR THE PREPARATION THEREOF

[75] Inventors: Shoji Tamai; Wataru Yamashita; Yuichi Okawa; Yuko Ishihara; Keizaburo Yamaguchi; Akihiro Yamaguchi, all of Kanagawa, Japan

[73] Assignee: Mitsui Toatsu Chemicals, Incorporated, Tokyo, Japan

[21] Appl. No.: 894,940

[22] Filed: Jun. 8, 1992

[30] Foreign Application Priority Data

Jun. 10, 1991 [JP] Japan .................. 3-137688
Jul. 1, 1991 [JP] Japan .................. 3-160199
Jul. 4, 1991 [JP] Japan .................. 3-164241

[51] Int. Cl.⁵ .............. C08G 73/10; C08G 69/26; C08G 8/02
[52] U.S. Cl. .................. 528/125; 528/126; 528/128; 528/171; 528/172; 528/173; 528/174; 528/176; 528/183; 528/185; 528/188; 528/220; 528/229; 528/350; 528/353
[58] Field of Search ............... 528/125, 126, 128, 171, 528/172, 173, 174, 176, 183, 188, 185, 220, 229, 350, 353

[56] References Cited

U.S. PATENT DOCUMENTS

3,959,350 5/1976 Rogers .................. 528/353
4,065,345 12/1977 Progar et al. .......... 528/353
4,959,440 9/1990 Tamai .................. 528/353

FOREIGN PATENT DOCUMENTS

200204 11/1986 European Pat. Off. .

OTHER PUBLICATIONS

CA 70(26):116221x.
CA 92(20):164327n.

Primary Examiner—John Kight, III
Assistant Examiner—P. Hampton-Hightower
Attorney, Agent, or Firm—Burns, Doane, Swecker & Mathis

[57] ABSTRACT

A heat-resistant and thermoplastic polyimide which has low dielectric characteristics and recurring structural units of the following formula

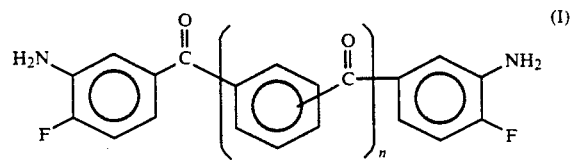

wherein R is a tetravalent radical having from 2 to 27 carbon atoms and selected from the group consisting of an aliphatic radical, alicyclic radical, monoaromatic radical, condensed polyaromatic radical and noncondensed aromatic radical connected each other with a direct bond or a bridge member; aromatic diamines which are useful for the raw material monomers of the polyimide and have following formulas:

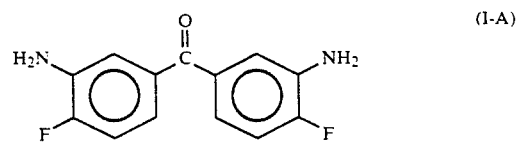

and

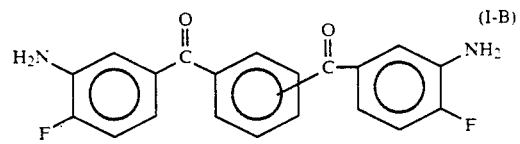

and a process for preparing the polyimide of the above formula by reacting these aromatic diamines with a tetracarboxylic dianhydride in the presence of an aromatic dicarboxylic anhydride or aromatic monoamine, and successively thermally or chemically imidizing the resultant polyamic acid.

21 Claims, 2 Drawing Sheets

POLYIMIDE AND PROCESS FOR THE PREPARATION THEREOF

BACKGROUND OF THE INVENTION

1. Field of the Invention

The present invention relates to a novel thermoplastic polyimide, aromatic diamine compound useful for the raw material monomer of the polyimide, and a process for preparating the polyimide. More particularly, the invention relates to a novel polyimide having excellent processability and a molecular structure useful for providing the polyimide with low dielectric characteristics, a process for preparing the polyimide and novel compounds 3,3'-diamino-4,4'-difluorobenzophenone and 1,3- or 1,4-bis(3-amino-4-fluorobenzoyl)benzene which are used for the raw material monomers of the polyimide.

The novel 3,3'-diamino-4,4'-difluorobenzophenone and 1,3- or 1,4-bis(3-amino-4-fluorobenzoyl)benzene are useful for the raw material monomers of the polyimide and additionally can be utilized as the raw materials of polyamide, polyamidimide, bismaleimide and epoxy resin, and can also be applied to hardeners of other maleimide compounds and epoxy compounds.

2. Related Art of the Invention

Recently, heat-resistant resin materials have been required to satisfy various performance such as flexibility as an ingredient of a composite and processability in addition to thermal and mechanical properties. Polyimide has focused attention as a material having these properties.

Polyimide is prepared by reaction of tetracarboxylic dianhydride with diamine. Conventionally known polyimide is excellent in mechanical strengths and dimensional stability in addition to substantially high heat-resistance and also has flame retardance and electrical insulation properties. Consequently, polyimide has already been widely used in the field where heat resistance is required, particularly in the field of electric and electronic equipment and is expected to be used in greater amounts and in other fields.

Various kinds of polyimide which exhibit excellent properties have already been developed. Conventionally known polyimide, however, has no distinct glass transition temperature, though excellent in heat resistance, and must be processed by such means as sinter molding in the case of being used as a molding material.

Other conventional polyimides are dissolved in halogenated hydrocarbon solvents, though excellent in processability, which leads to problems in solvent resistance. Thus, both merits and drawbacks have been simultaneously found in the properties of conventional polyimides. In order to extend the field of use for polyimides, disadvantages of polyimides have been improved or new properties have been provided for polyimides.

For example, a typical aromatic polyimide (Vespel) (Trade mark; E.I. Du Pont de Nemours & Co.) which is obtained by reacting 4,4'-diaminodiphenyl ether with pyromellitic dianhydride is insoluble and infusible and hence has the disadvantage that processing is difficult. Vespel powder is processed by a special method, sinter molding. Sinter molding, however, is difficult to provide molded articles having a complex shape and further requires a finishing operation of the molded articles in order to obtain precise products, which leads to a great disadvantage of an increase in processing cost.

On the other hand, a polyimide resin having a benzophenone skeleton in the molecular structure has been known to have excellent heat resistance, mechanical characteristics and adhesive strength. For example, polyimide resin (LARC-TPI) which is prepared from 3,3-diaminobenzophenone is thermoplastic in addition to these excellent properties. However, processability of the resin is not good in spite of its thermoplastic property. Recently, a method for increasing the molecular chain length has been employed as a means for improving such processability. Consequently, it is expected to obtain high performance polyimide resin having good processability by applying the method to the benzophenone skeleton. On the other hand, a polyimide structure derived from a monomer diamine compound having meta-located amino and carbonyl groups such as the above 3,3'-diaminobenzophenone is also effective as another means for improving the processability.

For example, Proga et al. have described thermoplastic polyimide for use in a heat resistant adhesive in U.S. Pat. No. 4,065,345. Ohta et al. have disclosed thermoplastic polyimide represented by the formula (VI):

(Japanese Laid-Open Patent Hei 2-018419).

The polyimide has a obtained a novel property, injection molding ability, by controlling the molecular weight of the polymer and blocking the reactive ends of the polymer chain. The polyimide is further required to have improved electrical properties such as low dielectric characteristics.

Introduction of a halogen radical into the aromatic ring has been known as an effective means for improving low dielectric characteristics of polyimide. Further, introduction of a halogen radical into the ortho position of an amino radical has been described in Chemical Abstracts, 70, 116221X. However, a diamine compound having a large halogen atom at the ortho position of an amino radical has a disadvantage that high molecular weight polymer is difficult to obtain because of steric hindrance. Thus, such kind of polyimide has not yet been developed.

SUMMARY OF THE INVENTION

One object of the present invention is to provide a thermoplastic polyimide which has excellent processability and good chemical resistance in addition to substantially excellent heat resistance of polyimide and also has a molecular structure favorable for low dielectric characteristics of polyimide and a process for preparing the polyimide.

Another object of the invention is to provide an aromatic diamine which is useful for the raw material of polyimide having low dielectric characteristics.

As a result of an intensive investigation in order to accomplish the above objects, the present inventors have carried out a novel preparation of 3,3'-diamino-4,4'-difluorobenzophenone having the formula (I-A):

and 1,3- or 1,4-bis(3-amino-4-fluorobenzoyl)benzene having the formula (I-B):

and have found that the polyimide prepared by using these aromatic diamine compounds as a monomer component is a thermoplastic polyimide having excellent processability without impairing the essential properties of polyimides and also has a molecular structure useful for providing a polyimide with low dielectric characteristics. Thus the present invention has been completed.

That is, one aspect of the invention is a polyimide having recurring structural units of the formula (II):

wherein R is a tetravalent radical having from 2 to 27 carbon atoms and selected from the group consisting of an aliphatic radical, alicyclic radical, monoaromatic radical, condensed polyaromatic radical and noncondensed aromatic radical connected to each other with a direct bond or a bridge member, and n is an integer of 0 or 1; a preparation process of the polyimide; a polyimide having the recurring structural units of the formula (II) and terminating the polymer chain with an aromatic radical which is substantially unsubstituted or substituted with a radical having no reactivity with amine or carboxylic acid anhydride; and a process for preparing the same.

Another aspect of the invention is an aromatic diamine compound which is useful as a raw material monomer of the polyimide and is represented by the formula (I):

wherein n is an integer of 0 or 1.

A more particular aspect of the invention is a polyimide having recurring structural units of the formula (II-A):

wherein R is the same as in the formula (II), or a polyimide having recurring structural units of the formula (II-B):

wherein R is the same as in the formula (II), and a polyimide having these recurring structural units and terminating the polymer chain with an aromatic radical which is substantially unsubstituted or substituted with a radical having no reactivity with amine or dicarboxylic anhydride.

A process for preparing the polyimide by reacting the aromatic diamine of the above formula (I), that is, the aromatic diamine primarily consisting of 3,3'-diamino-4,4'-difluorobenzophenone having the formula (I-A) or 1,3- or 1,4-bis(3-amino-4-fluorobenzoyl)benzene having the formula (I-B), with a tetracarboxylic dianhydride represented primarily by the formula (III):

wherein R is a tetravalent radical having from 2 to 27 carbon atoms and selected from the group consisting of an aliphatic radical, alicyclic radical, monoaromatic radical, condensed polyaromatic radical and noncondensed aromatic radical connected to each other with a direct bond or a bridge member, and successively by thermally or chemically imidizing the resultant polyamic acid; and a process for preparing the polyimide by reacting the aromatic diamine of the above formula (I) with the tetracarboxylic dianhydride represented primarily by the above formula (III) in the presence of an aromatic dicarboxylic anhydride represented by the formula (IV):

wherein $Z_1$ is a divalent radical having from 6 to 15 carbon atoms and selected from the group consisting of a monoaromatic radical, condensed polyaromatic radical, noncondensed aromatic radical connected to each other with a direct bond or a bridge member, or in the presence of an aromatic monoamine represented by the formula (V):

wherein $Z_2$ is a monovalent radical having from 6 to 15 carbon atoms and selected from the group consisting of a monoaromatic radical, condensed polyaromatic radical and noncondensed aromatic radical connected to each other with a direct bond or a bridge member, and successively by thermally or chemically imidizing the resultant polyamic acid.

Another aspect of the invention is the raw material monomer of the polyimide represented by the above formula (I), that is, 3,3'-diamino-4,4'-difluorobenzophenone of the above formula (I-A) or 1,3- or 1,4-bis(3-amino-4-fluorobenzoyl)benzene of the formula (I-B).

A further aspect of the invention is a polyimide having an inherent viscosity of from 0.01 to 3.0 dl/g which is measured at 35° C. in a solution containing 0.50 g of the polyimide powder and 100 ml of a solvent mixture composed of 9 parts by weight of p-chlorophenol and 1 part by weight of phenol, and a process for preparing the polyimide.

3,3'-Diamino-4,4'-difluorobenzophenone of the invention has two benzene rings which are connected each other with a carbonyl radical, two terminal amino radicals which are individually meta located to the carbonyl radical, and two fluoro radicals which are ortho located to the amino radicals, respectively.

Other 1,3- or 1,4-bis(3-amino-4-fluorobenzoyl)benzenes have three benzene rings which are connected to each other with two carbonyl radicals, two terminal amino radicals which are individually meta located to each carbonyl radical, and two fluoro radicals which are ortho located to the amino radicals, respectively.

Conventionally, introduction of an halogen radical into the ortho position to an amino radical is disadvantageous in that polymer is difficult to form. On the other hand, a fluorine atom has smaller size as compared with other halogen atoms and hence can form polymer even though a halogen radical is present on the aromatic ring or the fluoro radical is at the ortho position to an amino radical. Polyimide derived from the diamine has processability due to a folded structure of the polymer molecule and adhesive properties resulting from the carbonyl radical. Additionally, low dielectric characteristics can be expected from the fluoro radical as a halogen radical.

The aromatic diamine compound of the invention can be used for a raw material of polyimide, polyamide, polyamidimide, bismaleimide and epoxy resin, and additionally for a hardener of other maleimide compounds and epoxy compounds.

The polyimide of the invention prepared from the aromatic diamine compound as a raw material monomer is a novel polyimide having excellent processability, heat resistance and low dielectric characteristics. The polyimide is a thermoplastic polyimide having equivalent heat resistance compared to conventional polyimide and good processability at the same time. Thus, the polyimide is greatly expected for use in industry, particularly in the field of automobile parts, precision machinery members and space and aeronautic equipment.

The polyimide of the invention has lower dielectric characteristics as compared with polyimide derived from the diamine which has the same fundamental structure and is free from a fluorine atom in the molecular structure, for example, 1,3-bis(3-aminobenzoyl)benzene. Consequently, the polyimide of the invention can also be used in the field of electric and electronic industry.

DETAILED DESCRIPTION OF THE INVENTION

The polyimide of the invention has recurring structural units represented by the formula (II):

wherein R and n are the same as above, and practically has recurring structural units represented by the above formula (II-A) or (II-B).

Further, the polyimide of the formula (II-B) has recurring structural units of the formula (II-B-1):

(II-B-1)

wherein R is the same as above, or the formula (II-B-2):

(II-B-2)

wherein R is the same as above.

These polyimides are prepared from the aromatic diamine represented by the above formula (I) of the invention, that is, 3,3'-diamino-4,4'-difluorobenzophenone of the above formula (I-A) or 1,3- or 1,4-bis(3-amino-4-fluorobenzoyl)benzene of the formula (I-B).

These diamine compounds can be individually prepared by the following processes.

The aromatic diamine of the above formula (I-A), i.e., 3,3'-diamino-4,4'-difluorobenzophenone (hereinafter referred to as FDABP) is prepared by the following process.

FDABP can be prepared by reducing 3,3'-dinitro-4,4'-difluorobenzophenone. 3,3'-Dinitro-4,4'-fluorobenzophenone is a known compound and can be prepared, for example, by nitrating 4,4'-difluorobenzophenone (Chemical Abstracts, 92, 164327n).

Preparation of FDABP by reduction of 3,3'-dinitro-4,4'-difluorobenzophenone can, be carried out by a usual method for reducing a nitro radical to an amino radical, for example, the method described in Jikken Kagaku Koza, vol 15, Oxidation and Reduction (II), Published from Maruzen (1977). Exemplary methods include, reduction by iron powder and hydrochloric acid and catalytic reduction using a Raney catalyst or a noble metal catalyst having relatively low activity.

In the case of catalytic reduction, catalysts which can be used are metal catalysts generally used for catalytic reduction, and include, for example, nickel, palladium, platinum, rhodium, ruthenium, cobalt and copper.

Although these catalysts can also be used in the form of a metal, they are usually used by being supported on the surface of carriers such as carbon, barium sulfate, silica gel and alumina.

Reaction is usually carried out by using a solvent. No particular restriction is imposed upon the solvent as long as the solvent is inert in the reaction. Exemplary solvents which can be used for the reaction include methanol, ethanol, isopropyl alcohol and other alcohols; ethylene glycol, propylene glycol and other glycols; ether, dioxane, tetrahydrofuran, 2-methoxyethanol, ethylene glycol dimethyl ether, diethylene glycol dimethyl ether and other ethers; hexane, cyclohexane and other aliphatic hydrocarbons; benzene, toluene and other aromatic hydrocarbons; ethyl acetate, butyl acetate and other esters; and N,N-dimethylformamide, 1,3-dimethyl-2-imidazolidinone and other aprotic polar solvents. The solvents can be used singly or as a mixture.

No particular limitation is placed on the amount of these solvents. An amount of from 1 to 15 times the weight of the raw material is usually satisfactory.

No particular limitation is put on the reaction temperature. The reaction temperature is generally in the range of from 0° to 150° C., preferably from 10° to 80° C. in particular.

Reaction pressure is usually from atmospheric pressure to 50 kg/mm$^2$ . G.

Progress of the reaction can be inspected by the theoretical amount of hydrogen absorption, thin layer chromatography or high performance liquid chromatography. The reaction mixture thus obtained is hot-filtered or extracted to remove the catalyst and inorganic salts, and successively concentrated, if desired, to precipitate FDABP as crystals. Alternatively, hydrogen chloride gas can be blown into the reaction mixture after removing the catalyst and the inorganic salts to isolate hydrochloride of FDABP.

Other 1,3- or 1,4-bis(3-amino-4-fluorobenzoyl)benzene (hereinafter referred to as FABB) can be prepared by selective nitration of 1,3- or 1,4-bis(4-fluorobenzoyl)-benzene and successive reduction of resultant 1,3- or 1,4-bis(3-nitro-4-fluorobenzoyl) benzene. The 1,3- or 1,4-bis(4-fluorobenzoyl)benzene is a known compound and can be prepared, for example, by Friedel-Crafts' reaction of phthaloyl chloride with fluorobenzene as reported in Journal of Polymer Science, Part A; Polymer Chemistry, Vol. 125, 1093–1103(1987).

Nitration of 1,3- or 1,4-bis(4-fluorobenzoyl)benzene can be carried out by using mixed acid, fuming nitric acid, nitric acid-acetic acid, and other known nitrating agents. Mixed acid or fuming nitric acid is usually used. Using these nitrating agents, the reaction is carried out by the following procedures. In the case of nitrating with fuming nitric acid, from 80 to 98% nitric acid is used in an amount of from 4 to 12 moles per mole of the raw material. When mixed acid is used for nitration, the mixed acid composed of nitric acid or nitrate such as sodium or potassium nitrate and concentrated sulfuric acid is used in a mole ratio of the raw material: nitric acid or nitrate: concentrated sulfuric acid ranging 1:1.2:1–5.

The nitrating reaction can be carried out without any trouble in the presence of a halogenated hydrocarbon solvent such as methylene chloride, 1,2-dichloroethane, 1,1,2-trichloroethane, chloroform, carbon tetrachloride, 1,1,2,2-tetrachloroethane and trichloroethylene.

The reaction can be carried out by adding the raw material, 1,3- or 1,4-bis(4-fluorobenzoyl)benzene, to the nitrating agent, or by dropwise adding the nitrating agent to the raw material. When mixed acid is used, previously prepared mixed acid can be used, or the raw material is mixed with one component of the mixed acid and thereafter the other component of the mixed acid can be dropwise added to the resultant mixture.

Reaction temperature is in the range of from −10° to 80° C.

Reaction time is preferably in the range of from 2 to 10 hours.

After finishing the reaction, the reaction mixture is poured into a prescribed amount of ice water and the precipitate is filtered to obtain 1,3- or 1,4-bis(3-nitro-4- fluorobenzoyl)benzene. The product can be further purified by recrystallization.

Next, reduction of 1,3- or 1,4-bis(3-nitro-4-fluorobenzoyl) benzene to FABB can be carried out by conventional reduction procedures of reducing a nitro radical to an amino radical as used in the reduction of the above 3,3'-dinitro-4,4'-difluorobenzophenone.

That is, the reduction method, reducing catalyst used, various conditions of reducing reaction, reaction solvent, amount of the solvent, reaction temperature, reaction pressure and inspection of the progress of the reaction are the same as above.

The reaction mixture obtained is hot-filtered or extracted as above to remove the catalyst and inorganic salts, and successively concentrated, if desired, to precipitate FABB as crystals. Alternatively, hydrogen chloride gas can be blown into the reaction mixture after removing the catalyst and inorganic salts to isolate FABB in the form of hydrochloride.

The polyimide of the invention can be prepared by the following process from the aromatic diamine obtained above.

The aromatic diamine used is the above 3,3'-diamino-4,4'-difluorobenzophenone and 1,3- or 1,4bis(3-amino-4-fluorobenzoyl)benzene.

The tetracarboxylic dianhydride which is used for the other raw material monomer is generally represented by the formula (III):

(III)

wherein R is a tetravalent radical having from 2 to 27 carbon atoms and selected from the group consisting of an aliphatic radical, alicyclic radical, monoaromatic radical, condensed polyaromatic radical and noncondensed aromatic radical connected to each other with a direct bond or a bridge member.

In practice, R in the formula (III) is a tetravalent radical selected from the group consisting of an aliphatic radical having from 2 to 10 carbon atoms, alicyclic radical having from 4 to 10 carbon atoms, monoaromatic radical having the formula (a):

condensed polyaromatic radical having the formula (b):

and a noncondensed aromatic radical which is connected to each other with a direct bond or a bridge member and is represented by the formula (d):

wherein X is a direct bond, —CO—, —O—, —S—, —SO$_2$—, —CH$_2$—, —C(CH$_3$)$_2$—, —C(CF$_3$)$_2$—, or wherein Y is a direct bond, —CO—, —O—, —S—, —SO$_2$—, —CH$_2$—, —C(CH$_3$)$_2$— or —C(CF$_3$)$_2$—.

The polyimide of the invention can be prepared by reacting the above aromatic diamine with one or more tetracarboxylic dianhydrides and further dehydration-cyclizing the resulting polyamic acid.

Consequently, the polyimide of the invention is prepared by using the above 3,3'-diamino-4,4'-difluorobenzophenone or 1,3- or 1,4-bis(3-amino-4-fluorobenzoyl)-benzene as an aromatic diamine, i.e., a requisite raw material monomer. However, other aromatic diamines can also be used in combination as long as giving no adverse effect on the good properties of the polyimide.

Exemplary diamines which can be used in combination include, for example, m-phenylenediamine, o-phenylenediamine, p-phenylenediamine, m-aminobenzylamine, p-aminobenzylamine, 4,4'-diaminodiphenyl ether, 3,3'-diaminodiphenyl ether, 3,4'-diaminodiphenyl ether, bis(3-aminophenyl) sulfide, (3-aminophenyl)(4-aminophenyl) sulfide, bis(4-aminophenyl) sulfide, bis(3-aminophenyl) sulfoxide, (3-aminophenyl)(4-aminophenyl) sulfoxide, bis(4-aminophenyl) sulfoxide, bis(3-aminophenyl) sulfone, (3-aminophenyl)(4-aminophenyl) sulfone, bis(4-aminophenyl) sulfone, 3,3'-diaminobenzophenone, 3,4'-diaminobenzophenone, 4,4'-diaminobenzophenone, 3,3'-diaminodiphenylmethane, 3,4'-diaminodiphenylmethane, 4,4'-diaminodiphenylmethane, bis [4-(3-aminophenoxy)phenyl] methane, bis [4-(4-aminophenoxy)phenyl] methane, 1,1-bis [4-(3-aminophenoxy)phenyl] ethane, 1,1-bis [4-(4-aminophenoxy)phenyl] ethane, 1,2-bis [4-(3-aminophenoxy)phenyl] ethane, 1,2-bis [4-(4-aminophenoxy)phenyl] ethane, 1,2-bis [4-(3-aminophenoxy)phenyl] propane, 1,2-bis [4-(4-aminophenoxy)phenyl] propane, 2,2-bis [4-(3-aminophenoxy)phenyl] butane, 2,2-bis [3-(3-aminophenoxy)phenyl] -1,1,1,3,3,3-hexafluoropropane, 2,2-bis [4-(4-aminophenoxy)phenyl] -1,1,1,3,3,3-hexafluoropropane, 1,3-bis(3-aminophenoxy)benzene, 1,3-bis(4-aminophenoxy)benzene, 1,4-bis(3-aminophenoxy)benzene, 1,4-bis(4-aminophenoxy)benzene, 4,4'-bis(3-aminophenoxy)biphenyl, 4,4'-bis(4-aminophenoxy)biphenyl, bis [4-(3-aminophenoxy)phenyl] ketone, bis [4-(4-aminophenoxy)phenyl] ketone, bis [4-(3-aminophenoxy)phenyl] sulfide, bis [4-(4-aminophenoxy)phenyl] sulfide, bis [4-(3-aminophenoxy)phenyl] sulfoxide, bis [4-(4-aminophenoxy)phenyl] sulfoxide, bis [4-(3-aminophenoxy)phenyl] sulfone, bis [4-(4-aminophenoxy)phenyl] sulfone, bis [4-(3-aminophenoxy)phenyl] ether, bis [4-(4-aminophenoxy)phenyl] ether, 1,4-bis [4-(3-aminophenoxy)benzoyl] benzene, 1,3-bis [4-(3-aminophenoxy)benzoyl] benzene, 4,4'-bis [3-(4-aminophenoxy)benzoyl] diphenyl ether, 4,4'-bis [3-(3-aminophenoxy)benzoyl] diphenyl ether, 4,4'-bis [4-(4-amino-α,α-dimethylbenzyl)phenoxy] benzophenone, 4,4'-bis [4-(4-amino-α,α-dimethylbenzyl)phenoxy] diphenyl sulfone, bis [4- {4-(3-aminophenoxy)phenoxy} phenyl] sulfone, bis [4- {4-(4-aminophenoxy)phenoxy} phenyl] sulfone, 1,4-bis [4-(4-aminophenoxy)-α,α-dimethylbenzyl] benzene, and 1,3-bis [4-(4-aminophenoxy)-α,α-dimethylbenzyl] benzene. These aromatic diamines can be used singly or as a mixture.

Representative tetracarboxylic dianhydrides which can be used in the invention and represented by the formula (IV) include, for example, ethylenetetracarboxylic dianhydride, cyclopentanetetracarboxylic dianhydride, pyromellitic dianhydride, 3,3',4,4'-benzophenonetetracarboxylic dianhydride, 2,2',3,3'-benzophenonetetracarboxylic dianhydride, 3,3',4,4'-biphenyltetracarboxylic dianhydride, 2,2',3,3'-biphenyltetracarboxylic dianhydride, 2,2-bis(3,4-dicarboxyphenyl)propane dianhydride, 2,2-bis(2,3-dicarboxyphenyl)propane dianhydride, bis(3,4-dicarboxyphenyl)ether dianhydride, bis(3,4-dicarboxyphenyl) sulfone dianhydride, 1,1-bis(2,3-dicarboxyphenyl)ethane dianhydride, bis(2,3-dicarboxyphenyl)methane dianhydride, bis(3,4-dicarboxyphenyl)methane dianhydride, 2,2-bis(3,4-dicarboxyphenyl)-1,1,1,3,3,3-hexafluoropropane dianhydride, 2,2-bis(2,3-dicarboxyphenyl)-1,1,1,3,3,3-hexafluoropropane dianhydride, 2,3,6,7-naphthalenetetracarboxylic dianhydride, 1,4,5,8-naphthalenetetracarboxylic dianhydride, 1,2,5,6-naphthalenetetracarboxylic dianhydride, 1,2,3,4-benzenetetracarboxylic dianhydride, 3,4,9,10-perylenetetracarboxylic dianhydride, 2,3,6,7-anthracenetetracarboxylic dianhydride and 1,2,7,8-phenanthrenetetracarboxylic dianhydride. These tetracarboxylic dianhydrides can be used singly or as a mixture.

The polyimide of the invention is prepared by using the aromatic diamine and the tetracarboxylic dianhydride as monomer components and has recurring structural units represented primarily by the formula (II). The polyimide having recurring structural units primarily represented by the formula (II) and terminating the polymer chain with an aromatic radical which is unsubstituted or substituted with a radical having no reactivity with amine or dicarboxylic anhydride, and a composition comprising these polyimides are also included in the polyimide of the invention.

The polyimide having at the polymer chain and an aromatic radical which is unsubstituted or substituted with a radical having no reactivity with amine or dicarboxylic anhydride can be prepared by reacting the aromatic diamine of the above formula (I) with the tetracarboxylic dianhydride represented primarily by the above formula (III) in the presence of an aromatic dicarboxylic anhydride represented by the formula (IV):

(IV)

wherein $Z_1$ is a divalent radical having from 6 to 15 carbon atoms and selected from the group consisting of a monoaromatic radical, condensed polyaromatic radical, noncondensed aromatic radical connected to each other with a direct bond or a bridge member, or in the presence of an aromatic monoamine represented by the formula (V):

$$Z_2-NH_2 \qquad (V)$$

wherein $Z_2$ is a divalent radical having from 6 to 15 carbon atoms and selected from the group consisting of a monoaromatic radical, condensed polyaromatic radical, noncondensed aromatic radical connected to each other with a direct bond or a bridge member, and successively by thermally or chemically imidizing the resultant polyamic acid.

The aromatic dicarboxylic anhydrides which can be used in the process include, for example, phthalic anhydride, 2,3-benzophenonedicarboxylic anhydride, 3,4-benzophenonedicarboxylic anhydride, 2,3-dicarboxyphenyl phenyl ether anhydride, 2,3-biphenyldicarboxylic anhydride, 3,4-biphenyldicarboxylic anhydride, 2,3-dicarboxyphenyl phenyl sulfone anhydride, 3,4-dicarboxyphenyl phenyl sulfone anhydride, 2,3-dicarboxyphenyl phenyl sulfide anhydride, 3,4-dicarboxyphenyl phenyl sulfide anhydride, 1,2-naphthalenedicarboxylic anhydride, 2,3-naphthalenedicarboxylic anhydride, 1,8-naphthalenedicarboxylic anhydride, 1,2-anthracenedicarboxylic anhydride, 2,3-anthracenedicarboxylic anhydride, and 1,9-anthracenedicarboxylic anhydride. These dicarboxylic anhydrides can be substituted with a radical having no reactivity with amine or dicarboxylic anhydride.

In these dicarboxylic anhydrides, phthalic anhydride is most preferred in view of properties and practical use of resulting polyimide. The polyimide obtained is excellent in processing stability at high temperatures, has outstanding chemical resistance, and is very useful as a base material for space and aeronautic equipment and electric and electronic devices in view of the above excellent processability.

Phthalic anhydride can be partially replaced without any trouble by other dicarboxylic dianhydride as long as giving no adverse effect on the good properties of the polyimide.

The amount of dicarboxylic anhydride is in the range of from 0.001 to 1.0 mole per mole of the aromatic diamine of the formula (I). When the amount is less than 0.001 mole, melt viscosity is increased in high temperature processing and results in deteriorated processability. On the other hand, an amount exceeding 1.0 mole lowers mechanical characteristics of processed articles. Thus, preferred amount is in the range of from 0.01 to 0.5 mole.

Exemplary aromatic monoamines which can be used in the process include aniline, o-toluidine, m-toluidine, p-toluidine, 2,3-xylidine, 2,4-xylidine, 2,5-xylidine, 2,6-xylidine, 3,4-xylidine, 3,5-xylidine, o-chloroaniline, m- chloroaniline, p-chloroaniline, o-bromoaniline, m-bromoaniline, p-bromoaniline, o-nitroaniline, m-nitroaniline, p-nitroaniline, o-aminophenol, m-aminophenol, p-aminophenol, o-anisidine, m-anisidine, p-anisidine, o-phenetidine, m-phenetidine, p-phenetidine, o-aminobenzaldehyde, m-aminobenzaldehyde, p-aminobenzaldehyde, o-aminobenzonitrile, m-aminobenzonitrile, p-aminobenzonitrile, 2-aminobiphenyl, 3-aminobiphenyl, 4-aminobiphenyl, 2-aminophenyl phenyl ether, 3-aminophenyl phenyl ether, 4-aminophenyl phenyl ether, 2-aminobenzophenone, 3-aminobenzophenone, 4-aminobenzophenone, 2-aminophenyl phenyl sulfide, 3-aminophenyl phenyl sulfide, 4-aminophenyl phenyl sulfide, 2-aminophenyl phenyl sulfone, 3-aminophenyl phenyl sulfone, 4-aminophenyl phenyl sulfone, α-naphthylamine, β-naphthylamine, 1-amino-2-naphthol, 2-amino-1-naphthol, 4-amino-1-naphthol, 5-amino-1-naphthol, 5-amino-2-naphthol, 7-amino-2-naphthol, 8-amino-1-naphthol, 8-amino-7-naphthol, 8-amino-2-naphthol, 1-aminoanthracene, 2-aminoanthracene and 9-aminoanthracene. These aromatic monoamines can have a radical having no reactivity with amine or dicarboxylic anhydride.

The amount of aromatic monoamine is in the range of from 0.001 to 1.0 mole per mole of the tetracarboxylic dianhydride of the formula (III). When the amount is less than 0.001 mole, melt viscosity is increased in high temperature processing and results in deteriorated processability. On the other hand, an amount exceeding 1.0 mole lowers the mechanical characteristics of the processed articles. Thus, a preferred amount is in the range of from 0.01 to 0.5 mole.

Consequently, in the case of preparing the polyimide of the invention which has an unsubstituted or substituted aromatic radical at the polymer chain end, the mole ratio of the tetracarboxylic dianhydride, aromatic diamine and dicarboxylic anhydride or aromatic monoamine is in the range of from 0.9 to 1.0 mole of the aromatic diamine and from 0.001 to 1.0 mole of the dicarboxylic anhydride or the aromatic monoamine per mole of the tetracarboxylic dianhydride.

The mole ratio of aromatic diamine to tetracarboxylic dianhydride is usually adjusted in the preparation of polyimide in order to control the molecular weight of formed polyimide. In the process of the invention, a suitable mole ratio for providing polyimide having good melt flowability is in the range of from 0.9 to 1.0 mole of the aromatic diamine per mole of the tetracarboxylic dianhydride.

Any preparation process of polyimide including known processes can be applied to the preparation of the polyimide in the invention, and particularly preferred process is carried out in an organic solvent.

Exemplary organic solvents which can be used in the preparation include, N,N-dimethylformamide, N,N-dimethylacetamide, N,N-diethylacetamide, N,N-dimethylmethoxyacetamide, N-methyl-2-pyrrolidone, 1,3-dimethyl-2-imidazolidinone, N-methylcaprolactam, 1,2-dimethoxyethane, bis(2-methoxyethyl) ether, 1,2-bis(2-methoxyethoxy)ethane, bis [2-(2-methoxyethoxy)ethyl] ether, tetrahydrofuran, 1,3-dioxane, 1,4-dioxane, pyridine, picoline, dimethyl sulfoxide, dimethyl sulfone, tetramethylurea, hexamethylphosphoramide, phenol, o-cresol, m-cresol, p-cresol, p-chlorophenol, anisole, benzene, toluene and xylene. These solvents can be used singly or as a mixture.

In the process of the invention, the aromatic diamine, tetracarboxylic dianhydride and aromatic dicarboxylic anhydride or aromatic monoamine can be added to the organic solvent by any one of the following methods.

(A) After reacting tetracarboxylic dianhydride with aromatic diamine, aromatic dicarboxylic anhydride or aromatic monoamine is added to continue the reaction.

(B) After reacting aromatic diamine with aromatic dicarboxylic anhydride, tetracarboxylic dianhydride is added to continue the reaction.

(C) After reacting tetracarboxylic dianhydride with aromatic monoamine, aromatic diamine is added to continue the reaction.

(D) Tetracarboxylic dianhydride, aromatic diamine and aromatic dicarboxylic anhydride or aromatic monoamine are added and reacted at the same time.

Reaction temperature is usually 250° C. or less, preferably 50° C. or less. No particular restriction is imposed upon the reaction pressure. The reaction can be satisfactorily carried out under atmospheric pressure. Reaction time differs depending upon the tetracarboxylic acid anhydride, solvent and reaction temperature, and is usually from 4 to 24 hours.

The resulting polyamic acid is thermally imidized by heating at 100° to 400° C. or chemically imidized by using an imidizing agent such as acetic anhydride to obtain polyimide having recurring units corresponding to the polyamic acid.

Alternatively, the aromatic diamine and tetracarboxylic dianhydride, and further the aromatic dicarboxylic anhydride or aromatic monoamine in the case of terminating the polyimide polymer chain with an aromatic radical, are dissolved in a solvent, and thereafter formation of polyamic acid precursor and imidization of the polyamic acid can be simultaneously carried out by heating the resulting solution to obtain the desired polyimide.

That is, a film or the powder of polyimide can be prepared by conventionally known methods.

The particularly preferred polyimide obtained above has an inherent viscosity of from 0.01 to 3.0 dl/g which is measured at 35° C. in a solution containing 0.5 g of the polyimide powder and 100 ml of a solvent mixture composed of 9 parts by weight of p-chlorophenol and 1 part of phenol.

In the melt processing of the polyimide of the invention, other thermoplastic resins such as polyethylene, polypropylene, polycarbonate, polyarylate, polyamide, polysulfone, polyether sulfone, polyether ketone, polyphenylene sulfide, polyamideimide, polyetherimide, modified polyphenylene oxide and polyimide, the polyimide of the invention exclusive, can also be blended depending upon the object for use in the range giving no adverse effect on the good properties of the polyimide of the invention.

Various additives used for common resin compositions can be used so long as not impairing the object of the invention. The additives which can be used include, for example, graphite, carborundum, silica powder, molybdenum disulfide, fluororesin and other abrasion resistance improvers; glass fiber, carbon fiber and other reinforcements; antimony trioxide, magnesium carbonate, calcium carbonate and other flame retardants; clay, mica and other electrical property improvers; asbestos, silica, graphite and other tracking resistance improvers; iron powder, zinc powder, aluminum powder, copper powder and other thermal conductivity improvers; and other miscellaneous materials such as glass beads, glass balloons, talc, diatomaceous earth, alumina, silicate balloons, hydrated alumina, metal oxides and colorants.

Further, the polyimide of the invention can be used in the form of filaments in addition to various types of molded articles and films. Other various examples of usage include a composite material obtained by impregnating the polyimide of the invention to fibrous cloth composed of fibers such as carbon fiber, copper clad circuit substrate obtained by coating the polyimide on metal foils such as copper foil and metal plates, and multi-layered film and covering film obtained by coating the polyimide on various polymer films.

The present invention will hereinafter be illustrated in detail by way of examples.

The properties of the polyimide in the examples were measured by the following method.

Tg, Tc, Tm:
Measured with Shimadzu DT-40 Series, DSC-41M.
5% weight-loss Temperature:
Measured with DTG (Shimadzu DT-40 Series, DTG-40M).
Melt Viscosity:
Measured with a Shimadzu Koka Type Flow Tester (CFT-500A) under 100 kg load.
Dielectric Constant:
Measured in accordance with ASTM D 150-87.

EXAMPLE 1

To a reaction vessel equipped with a stirrer, reflux condenser, water separator and a nitrogen inlet tube, 24.8 g (0.1 mole) of 3,3'-diamino-4,4'-difluorobenzophenone, 30.91 g (0.096 mole) of 3,3',4,4'-benzophenonetetracarboxylic dianhydride, 1.184 g ($8 \times 10^{-3}$ mole) of phthalic anhydride, 1.4 g of picoline and 228 g of m-cresol were charged and heated to 145° C. with stirring in the nitrogen atmosphere while distilling out about 3.5 cc of water. The mixture was further reacted for 4 hours at 140° to 150° C. Thereafter, the reaction mixture was cooled to room temperature and poured into 15 l methyl ethyl ketone. The precipitated powder was filtered, washed with methyl ethyl ketone and dried at 180° C. for 24 hours under reduced pressure to obtain 52.2 g (98% yield) of polyimide powder having an inherent viscosity of 0.45 dl/g. The inherent viscosity was measured at 35° C. by heat-dissolving 0.5 g of the polyimide powder in 100 ml of a solvent mixture of p-chlorophenol and phenol in a ratio of 9/1 by weight.

Figure 1:
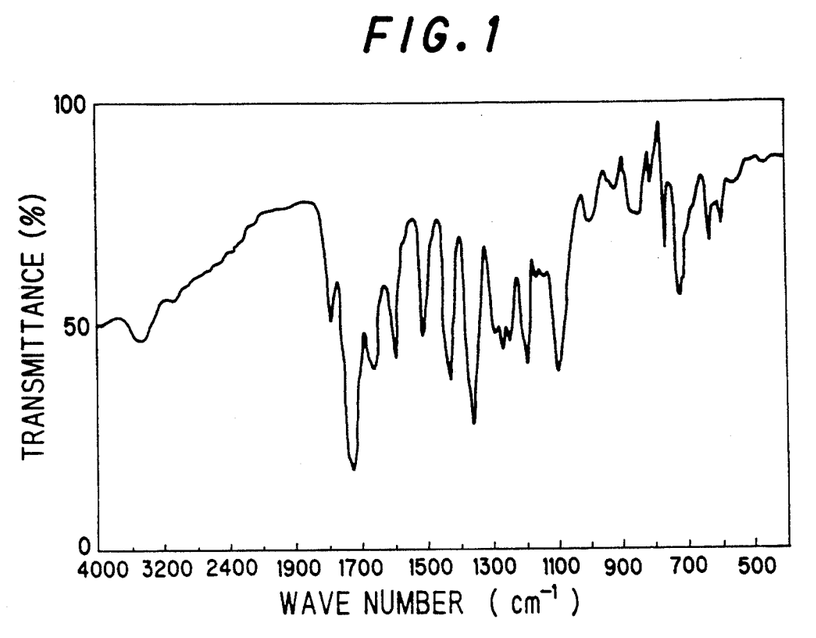
FIG. 1 is a drawing illustrating the IR absorption spectrum of the polyimide powder obtained in Example 1.

The polyimide had a glass transition temperature (Tg) of 259° C. and a 5% weight loss temperature of 554° C. in the air. The IR absorption spectrum of the polyimide powder is illustrated in FIG. 1. In the spectrum atlas, the characteristic absorption band of imide was distinctly observed in the wave lengths of around 1780 cm$^{-1}$ and 1720 cm$^{-1}$. Following results were obtained in elemental analysis of the polyimide powder.

| | Elemental analysis | | | |
|---|---|---|---|---|
| | C | H | N | F |
| Calculated (%) | 67.4 | 2.26 | 5.25 | 7.12 |
| Found (%) | 67.3 | 2.25 | 5.21 | 7.14 |

The polyimide powder was insoluble in methylene chloride, chloroform and other halogenated hydrocarbons.

Figure 2:
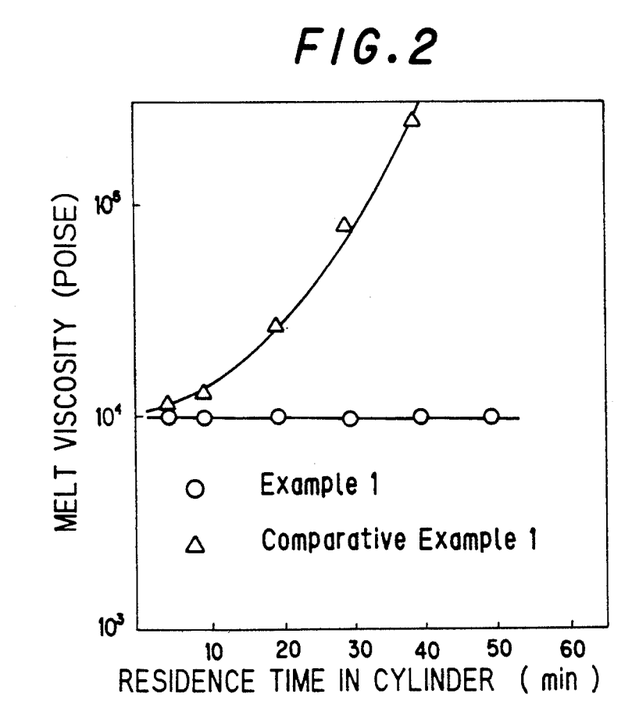
FIG. 2 illustrates relationships between melt viscosity change and residence time in the cylinder of a flow tester on the polyimide obtained in Example 1 and Comparative Example 1.
Figure 3:
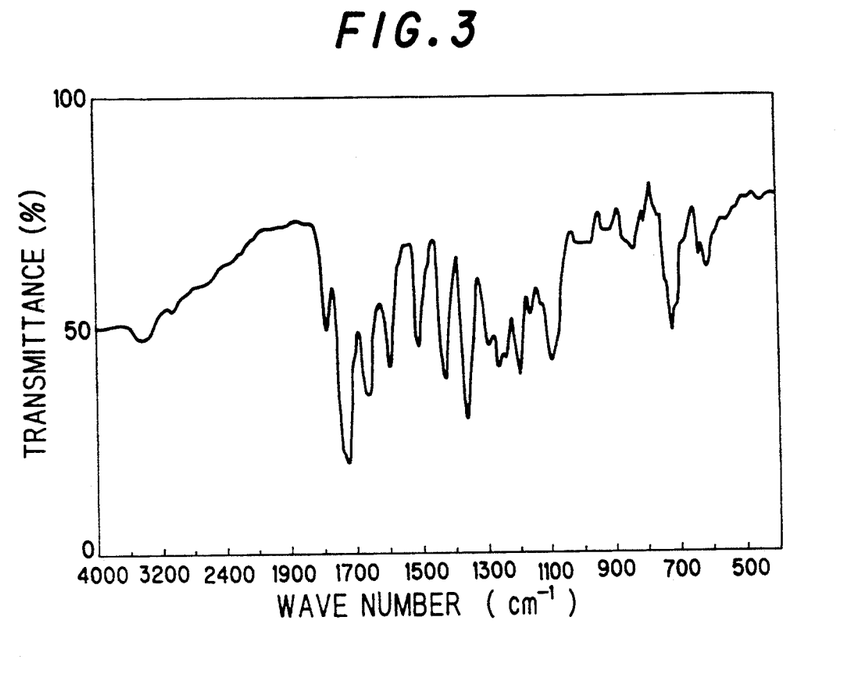
FIG. 3 is a drawing illustrating the IR absorption spectrum of the polyimide powder obtained in Example 11.

Melt viscosity of the polyimide was measured with a Koka type flow tester under 100 kg load by using an orifice having a diameter of 0.1 cm and a length of 1 cm. The melt viscosity was 9800 poise at 370° C. and the strand obtained was brown, transparent and very flexible. Stability of the polyimide in processing was measured by changing the residence time in the cylinder of the flow tester at 370° C. under a load of 100 kg. Results are illustrated in FIG. 2. The melt viscosity was almost constant although residence time in the cylinder was extended, and the polyimide was proved to have good heat stability.

COMPARATIVE EXAMPLE 1

The same procedures as conducted in Example 1 were carried out without using phthalic anhydride to obtain 50.8 g (97.5% yield) of polyimide powder. The polyimide powder had an inherent viscosity of 0.44 dl/g, glass transition temperature of 258° C. and a 5% weight loss temperature of 558° C. in the air. The stability of the polyimide in processing was measured with the flow tester by carrying out the same procedures as Example 1. Results are illustrated in FIG. 2. Melt viscosity of the polyimide was increased with extended residence time in the cylinder. The polyimide had inferior heat stability as compared with the polyimide obtained in Example 1.

EXAMPLES 2-5

The same procedures as conducted in Example 1 were carried out except that tetracarboxylic dianhydrides illustrated in Table 1 were used in an amount shown in Table 1. The yield, inherent viscosity, Tg, 5% weight loss temperature and elemental analysis of the polyimides obtained are summarized in Table 1.

TABLE 1

| Example | Diamine compound | tetra-carboxylic dianhydride | Yield (%) | Inherent viscosity (dl/g) |
|---|---|---|---|---|
| 2 | 3,3'-Diamino-4,4'-difluoro-benzophenone 24.8 g (0.1 mole) | BPDA*1 28.22 g (0.096 mole) | 98.5 | 0.44 |
| 3 | 3,3'-Diamino-4,4'-difluoro-benzophenone 24.8 g (0.1 mole) | 6 FDA*2 42.62 g (0.096 mole) | 98.3 | 0.43 |
| 4 | 3,3'-Diamino-4,4'-difluoro-benzophenone 24.8 g (0.1 mole) | ODPA*3 29.76 g (0.096 mole) | 98.6 | 0.47 |
| 5 | 3,3'-Diamino-4,4'-difluoro-benzophenone 24.8 g (0.1 mole) | HQDA*4 38.59 g (0.096 mole) | 98.0 | 0.46 |

| 5% weight loss temperature (°C.) | | Elemental analysis (°C.) | | | |
|---|---|---|---|---|---|
| | | C | H | N | F |
| 560 | Calculated | 68.76 | 2.39 | 5.53 | 7.51 |
| | Found | 68.75 | 2.33 | 5.49 | 7.53 |
| 553 | Calculated | 58.85 | 1.86 | 4.31 | 22.68 |
| | Found | 58.87 | 1.88 | 4.29 | 22.59 |
| 554 | Calculated | 66.48 | 2.69 | 5.35 | 7.26 |
| | Found | 66.50 | 2.65 | 5.34 | 7.26 |
| 551 | Calculated | 68.41 | 2.61 | 4.59 | 6.23 |
| | Found | 68.42 | 2.61 | 4.56 | 6.21 |

Note:
*1 3,3',4,4'-Biphenyltetracarboxylic dianhydride
*2 2,2-Bis(3,4-dicarboxyphenyl)-1,1,1,3,3,3-hexafluoropropane dianhydride
*3 3,3',4,4'-Diphenylethertetracarboxylic dianhydride
*4 4,4-(p-Phenylenedioxy)diphthalic dianhydride

EXAMPLE 6

To a reaction vessel equipped with a stirrer, reflux condenser and a nitrogen inlet tube, 24.8 g (0.1 mole) of 3,3'-diamino-4,4'-difluorobenzophenone and 170.0 g of N,N-dimethylacetamide were charged and 31.88 g (0.099 mole) of 3,3',4,4'-benzophenonetetracarboxylic dianhydride was added by portions in a nitrogen atmosphere with caution to prevent temperature rise of the solution and stirred for about 40 hours at room temperature.

The polyamic acid thus obtained had an inherent viscosity of 0.60 dl/g, which was measured at 35° C. in a N,N-dimethylacetamide solution having a concentration of 0.5 g /100 ml. A portion of the polyamic acid solution was cast on a glass plate and heated at 100° C., 200° C. and 300° C. each for an hour to obtain a polyimide film having a thickness of 50 μm. The polyimide film obtained had a tensile strength of 15.6 kg/mm$^2$, tensile modulus of 390 kg/mm$^2$ and elongation of 7.0% in accordance with ASTM D-822. The dielectric constant of the polyimide film was 3.57 at frequency of 60 Hz and 3.29 at 1 MHz.

COMPARATIVE EXAMPLE 2

Polyamic acid was prepared by carrying out the same procedures as conducted in Example 1 except that 24.8 g (0.1 mole) of 3,3'-diamino-4,4'-difluorobenzophenone was replaced by 22.2 g (0.1 mole) of 3,3'-diaminobenzophenone. A polyimide film having a thickness of 50 μm was prepared by carrying out the same procedures as conducted in Example 1. The film had a dielectric constant of 3.71 at frequency of 60 Hz and 3.67 at 1 MHz.

EXAMPLES 7-10

The same procedures as conducted in Example 6 were carried out by using the tetracarboxylic dianhydrides illustrated in Table 2 in amounts shown in Table 2 to obtain polyamic acids. Solutions of these polyamic acids were cast into corresponding polyimide films by carrying out the same procedures as conducted in Example 6.

The inherent viscosity of these polyamic acids and the dielectric constant of polyimide films obtained are illustrated in Table 2.

TABLE 2

| Example | Diamine compound | Tetra-carboxylic dianhydride | Inherent viscosity (dl/g) | Dielectric constant 60 Hz | Dielectric constant 1 MHz |
|---|---|---|---|---|---|
| 7 | 3,3'-diamino-4,4'-difluoro-benzophenone 24.8 g (0.1 mole) | BPDA*$^1$ 29.11 g (0.099 mole) | 0.62 | 3.56 | 3.41 |
| 8 | 3,3'-diamino-4,4'-difluoro-benzophenone 24.8 g (0.1 mole) | 6 FDA*$^2$ 43.96 g (0.099 mole) | 0.51 | 3.29 | 3.09 |
| 9 | 3,3'-diamino-4,4'-difluoro-benzophenone 24.8 g (0.1 mole) | OPDA*$^3$ 30.69 g (0.099 mole) | 0.55 | 3.49 | 3.38 |
| 10 | 3,3'-diamino-4,4'-difluoro-benzophenone 24.8 g (0.1 mole) | HQDA*$^4$ 30.80 g (0.099 mole) | 0.57 | 3.55 | 3.46 |

Note.
*$^1$3,3',4,4'-Biphenyltetracarboxylic dianhydride
*$^2$2,2-Bis(3,4-dicarboxyphenyl)-1,1,1,3,3,3-dianhydride
*$^3$3,3',4,4'-Diphenylethertetracarboxylic dianhydride
*$^4$4,4-(p-Phenylenedioxy)diphthalic dianhydride

EXAMPLE 11

To the same reaction vessel as used in Example 1, 35.2 g (0.1 mole) of 1,3-bis(3-amino-4-fluorobenzoyl)-benzene, 31.56 g (0.098 mole) of 3,3',4,4'-benzophenonetetracarboxylic dianhydride, 0.592 g (4 ×10$^{-3}$ mole) of phthalic anhydride, 1.4 g of γ-picoline and 269 g of m-cresol were charged and heated to 145° C. with stirring in a nitrogen atmosphere while distilling out 3.5 cc of water. The reaction was further continued for 4 hours at 140° to 150° C. The reaction mixture was then cooled to room temperature and poured into 1.5 l of methyl ethyl ketone. The precipitate was filtered, washed with methyl ethyl ketone and dried at 180° C. for 24 hours under reduced pressure to obtain 62.8 g (98.5% yield) of polyimide powder.

The polyimide powder obtained had an inherent viscosity of 0.45 dl/g. The inherent viscosity was measured at 35° C. in a solution containing 0.50 g of the polyimide powder in 100 ml of a solvent mixture consisting of p-chlorophenol and phenol in a ratio of 90:10 by weight. The polyimide powder had a glass transition temperature of 235° C. which was measured by DSC and a 5% weight loss temperature of 554° C. in the air. The IR absorption spectrum of the polyimide powder is illustrated in Table 3. In the spectrum atlas, remarkable absorption is observed around 1780 cm$^{-1}$ and 1720 cm$^{-1}$ which are characteristic absorption bands of imide.

Following results were obtained on the elemental analysis of the polyimide powder obtained.

| | Elemental analysis | | | |
|---|---|---|---|---|
| | C | H | N | F |
| Calculated (%) | 69.61 | 2.52 | 4.39 | 5.96 |
| Found (%) | 69.63 | 2.49 | 4.41 | 5.95 |

Further, the melt viscosity of the polyimide was measured with a Koka type flow tester under a load of 100 kg by using an orifice having a diameter of 0.1 cm and a length of 1 cm. The melt viscosity was 5700 poise at 380° C. The strand obtained was brown, transparent and very flexible. The processing stability of the polyimide was measured at 380° C. under 100 kg load by changing the residence time in the cylinder of the flow tester. Results are illustrated in Table 4.

Heat stability was good because melt viscosity was almost constant even though the residence time in the cylinder was extended.

COMPARATIVE EXAMPLE 13

Figure 4:
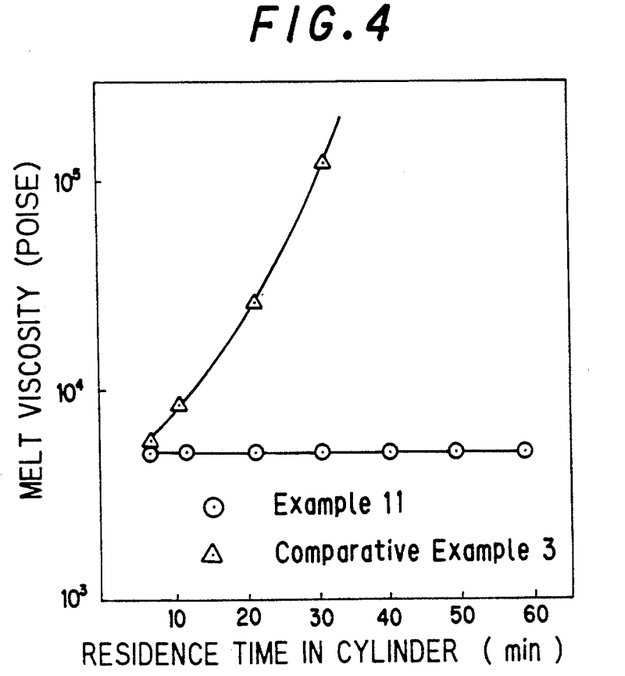
FIG. 4 illustrates relationships between melt viscosity change and residence time in the cylinder of a flow tester on the polyimide obtained in Example 11 and Comparative Example 3.

The same procedures as conducted in Example 11 were carried out without using phthalic anhydride to obtain 61.9 g (98% yield) of polyimide powder. The polyimide powder obtained had an inherent viscosity of 0.44 dl/g, glass transition temperature of 235° C. and a 5% weight loss temperature of 550° C. in the air. The processing stability of the polyimide was measured with the flow tester by the same procedures as carried out in Example 11. Results are illustrated in FIG. 4. The melt viscosity of the polyimide thus obtained was increased with prolonged residence time in the cylinder and proved to have inferior processing stability as compared with the polyimide obtained in Example 11.

EXAMPLES 12-16

The same procedures as conducted in Example 11 were carried out by using tetracarboxylic dianhydrides illustrated in Table 3 in amounts illustrated in Table 3 to obtain corresponding polyimide powder. The yield, inherent viscosity $\eta$, glass transition temperature Tg, 5% weight loss temperature Td(5.0) and elemental analysis of the polyimide powder are illustrated in Table 3.

TABLE 3

| Example | Diamine compound g(mole) | Tetra-carboxylic dianhydride g(mole) | Yield (%) | $\eta$ (dl/g) | Tg (°C.) |
|---|---|---|---|---|---|
| 12 | 1,3-bis(3-amino-4-fluorobenzoyl)benzene 35.2 (0.1) | PMDA*2 21.34 (0.098) | 98.5 | 0.46 | 268 |
| 13 | 1,3-bis(3-amino-4-fluorobenzoyl)benzene 35.2 (0.1) | BPDA*3 28.81 (0.098) | 98.5 | 0.44 | 248 |
| 14 | 1,3-bis(3-amino-4-fluorobenzoyl)benzene 35.2 (0.1) | 6 FDA*4 43.51 (0.098) | 98.3 | 0.43 | 237 |
| 15 | 1,3-bis(3-amino-4-fluorobenzoyl)benzene 35.2 (0.1) | ODPA*5 28.34 (0.098) | 98.6 | 0.45 | 226 |
| 16 | 1,3-bis(3-amino-4-fluorobenzoyl)benzene 35.2 (0.1) | HQDA*6 39.39 (0.098) | 98.0 | 0.46 | 212 |

| Td (5.0)*1 (°C.) | | Elemental analysis (%) | | | |
|---|---|---|---|---|---|
| | | C | H | N | F |
| 560 | Calculated | 67.48 | 2.27 | 5.23 | 7.09 |
| | Found | 67.44 | 2.23 | 5.26 | 7.01 |
| 561 | Calculated | 70.82 | 2.63 | 4.59 | 6.23 |
| | Found | 70.79 | 2.62 | 4.61 | 6.25 |
| 553 | Calculated | 61.12 | 2.15 | 3.75 | 20.09 |
| | Found | 61.14 | 2.18 | 3.73 | 20.01 |
| 550 | Calculated | 69.04 | 2.56 | 4.47 | 6.07 |
| | Found | 69.02 | 2.51 | 4.49 | 6.03 |
| 551 | Calculated | 70.20 | 2.79 | 3.91 | 5.31 |
| | Found | 70.18 | 2.76 | 3.93 | 5.34 |

Note.
*1 5% weight loss temperature
*2 Pyromellitic dianhydride
*3 3,3',4,4'-Biphenyltetracarboxylic dianhydride
*4 2,2-Bis(3,4-dicarboxyphenyl)-1,1,1,3,3,3-hexafluoropropane dianhydride
*5 3,3',4,4'-Diphenylethertetracarboxylic dianhydride
*6 4,4-(p-Phenylenedioxy)diphthalic dianhydride

EXAMPLE 17

To the same reaction vessel as used in Example 1, 35.2 g (0.1 mole) of 1,3-bis(3-amino-4-fluorobenzoyl)benzene and 227.1 g of N,N-dimethylacetamide were charged, and 21.5 g (0.099 mole) of pyromellitic dianhydride was added by portions in a nitrogen atmosphere with caution to prevent temperature rise of the solution and stirred for 40 hours at the room temperature. The polyamic acid thus obtained had an inherent viscosity of 0.60 dl/g. The inherent viscosity was measured at 35° C. in a N,N-dimethylacetamide solution at a concentration of 0.5 g/100 ml solvent. A portion of the polyamic acid solution was cast on a glass plate and heated at 100° C., 200° C. and 300° C. each for an hour to obtain a polyimide film having a thickness of 50 μm.

The polyimide film had a tensile strength of 13.8 kg/mm², tensile modulus of 320 kg/mm² and elongation of 7.0% in accordance with ASTM D-822. The polyimide film had a dielectric constant of 3.70 at frequency of 60 Hz and 4.30 at 1 MHz.

EXAMPLES 18-22

The same procedures as conducted in Example 17 were carried out by using tetracarboxylic dianhydrides illustrated in Table 4 in amounts shown in Table 4 to prepare corresponding polyamic acids. The polyamic acid solutions thus obtained were treated by the same procedures as conducted in Example 17 to obtain corresponding polyimide films. The inherent viscosity of the polyamic acids and the dielectric constant of polyimide films are illustrated in Table 4.

TABLE 4

| Example | Diamine compound g(mole) | Tetra-carboxylic dianhydride g(mole) | Inherent viscosity $\eta$ (dl/g) | Dielectric constant | |
|---|---|---|---|---|---|
| | | | | 60 Hz | 1 MHz |
| 18 | 1,3-bis(3-amino-4-fluorobenzoyl)benzene 35.2 (0.1) | BTDA*1) 31.88 (0.099) | 0.59 | 3.50 | 3.37 |
| 19 | 1,3-bis(3-amino-4-fluorobenzoyl)benzene 35.2 (0.1) | BPDA*2) 29.11 (0.099) | 0.61 | 3.65 | 3.45 |
| 20 | 1,3-bis(3-amino-4-fluorobenzoyl)benzene 35.2 (0.1) | 6 FDA*3) 43.96 (0.099) | 0.51 | 3.29 | 3.11 |
| 21 | 1,3-bis(3-amino-4-fluorobenzoyl)benzene 35.2 (0.1) | ODPA*4) 30.69 (0.099) | 0.55 | 3.45 | 3.39 |
| 22 | 1,3-bis(3-amino-4-fluorobenzoyl)benzene 35.2 (0.1) | HQDA*5) 39.80 (0.099) | 0.53 | 3.47 | 3.38 |

Note.
*1) 3,3',4,4'-Benzophenonetetracarboxylic dianhydride
*2) 3,3',4,4'-Biphenyltetracarboxylic dianhydride
*3) 2,2-Bis(3,4-dicarboxyphenyl)-1,1,1,3,3,3-hexafluoropropane dianhydride
*4) 3,3',4,4'-Diphenylethertetracarboxylic dianhydride
*5) 4,4-(p-Phenylenedioxy)diphthalic dianhydride

EXAMPLE 23

To a glass reaction vessel equipped with a thermometer and stirrer, 193 g (0.6 mole) of 1,3-bis(4-fluorobenzoyl)benzene and 509.6 g (5.04 mole) of 98% sulfuric acid were charged and cooled to an internal temperature of 10° C. with stirring. Successively, 105.5 g (1.44 mole) of 86% fuming nitric acid was added dropwise over 2 hours while maintaining the internal temperature from 8° to 15° C. After finishing dropwise addition, reaction was continued for 2 hours with stirring.

The reaction mixture was poured into 3 l of ice water. Precipitated crude crystals of 1,3-bis(3-nitro-4-fluorobenzoyl)benzene was filtered, washed with water, dried and recrystallized from 2-methoxyethanol to obtain 215.8 g (87.3% yield) of 1,3-bis(3-nitro-4-fluorobenzoyl)benzene. The recrystallized product had purity of 99.2% by high performance liquid chromatography and a melting point of 147.6°-149.4° C.

Next, a glass reaction vessel equipped with a stirrer, reflux condenser and a thermometer was charged with 82.4 g (0.2 mole) of the above 1,3-bis(3-nitro-4-fluorobenzoyl) benzene, 820 ml of a 80% aqueous ethanol solution and 82.0 g (1.46 mole) of iron powder were charged and the internal temperature was raised to 65° C. Successively, a solution containing 6.08 g of 36% hydrochloric acid in 80 ml of 80% ethanol was added dropwise over 2 hours and the reaction was continued further for an hour with stirring. The reaction mixture was cooled to room temperature and filtered. The residue obtained was dissolved in 280 g of hot 2-methoxyethanol and hot filtered to remove iron powder. The filtrate was poured into 2 l of water. The precipitated crystals were filtered, washed with water and dried to obtain 63.5 g of crude crystals of 1,3-bis(3-amino-4-fluorobenzoyl) benzene. The crude crystals were mixed with 120 ml of water, 36% hydrochloric acid and activated carbon, and dissolved by heating. The solution was hot filtered. To the filtrate, 12 g of sodium chloride was added and dissolved. The solution thus obtained was gradually cooled to precipitate 1,3-bis(3-amino-4-fluorobenzoyl)benzene hydrochloride. The hydrochloride was filtered and neutralized in water with a 28% aqueous ammonia solution to obtain 58.4 g (83.0% yield) of 1,3-bis(3-amino-4-fluorobenzoyl)benzene. The purified product had purity of 99.1% by high performance liquid chromatography and a melting point of 169.7°–170.7° C.

|  | Elemental analysis | | | |
|---|---|---|---|---|
|  | C | H | N | F |
| Calculated (%) | 68.2 | 4.0 | 8.0 | 10.8 |
| Found (%) | 67.1 | 4.1 | 7.8 | 11.0 |

EXAMPLE 24

To a glass reaction vessel equipped with a thermometer and stirrer, 161 g (0.5 mole) of 1,4-bis(4-fluorobenzoyl)benzene and 424.3 g (4.2 mole) of 97% sulfuric acid were charged and cooled to an internal temperature of 10° C. with stirring. Successively, 87.9 g (1.2 mole) of 86% fuming nitric acid was added dropwise over 2 hours while maintaining the internal temperature from 7° to 15° C. After finishing dropwise addition, reaction was continued for 2 hours with stirring.

The reaction mixture was poured into 3 l of ice water. Precipitated crude crystals of 1,4-bis(3-nitro-4-fluorobenzoyl)benzene were filtered, washed with water, dried and recrystallized from N,N-dimethylformamide to obtain 172.4 g (83.7% yield) of 1,4-bis(3-nitro-4-fluorobenzoyl)benzene. The recrystallized product had purity of 99.3% by high performance liquid chromatography and a melting point of 221.4°–222.6° C.

Next, a glass reaction vessel equipped with a stirrer, reflux condenser and a thermometer was charged with 41.2 g (0.1 mole) of the above 1,4-bis(3-nitro-4-fluorobenzoyl)benzene, 370 g of a 70% aqueous 2-methoxyethanol solution and 67 g of iron powder were charged and internal temperature was raised to 80° C. Successively, a solution containing 2.1 g of 36% hydrochloric acid in 40 g of 70% 2-methoxyethanol was added dropwise over 2 hours and the reaction was continued further for 3 hours with stirring. The reaction mixture was cooled to the room temperature and filtered. The residue obtained was dissolved in 176 g of hot 2-methoxyethanol and hot filtered to remove iron powder. The filtrate was poured into 2 l of water. The precipitated crystals were filtered, washed with water and dried to obtain 28.6 g of crude crystal of 1,4-bis(3-amino-4-fluorobenzoyl)benzene.

The crude crystals were purified by the same procedures as conducted in Example 23 to obtain 26.5 g (75.2% yield) of 1,4-bis(3-amino-4-fluorobenzoyl)benzene.

The purified product had purity of 98.2% by high performance liquid chromatography and a melting point of 219.9°–221.1° C.

|  | Elemental analysis | | | |
|---|---|---|---|---|
|  | C | H | N | F |
| Calculated (%) | 68.2 | 4.0 | 8.0 | 10.8 |
| Found (%) | 67.2 | 4.2 | 7.9 | 11.7 |

EXAMPLE 25

To a glass reaction vessel equipped with a stirrer, reflux condenser and a thermometer, 124 g (0.4 mole) of 3,3'-dinitro-4,4'-difluorobenzophenone, 1100 ml of a 80% aqueous ethanol solution and 280 g (5.0 mole) of iron powder were charged and the internal temperature was raised to 75° C. Successively, a solution containing 10.5 g of 36% hydrochloric acid in 124 ml of 80% ethanol was added dropwise and the reaction was further continued for 3 hours with stirring. After finishing the reaction, the reaction mixture was filtered at the same temperature and the filtrate was poured into 2 l of water. The precipitated crystal was filtered, washed with water and dried to obtain 90.5 g of crude crystals of 3,3'-diamino-4,4'-difluorobenzophenone. The crude crystal was mixed with 180 ml of water, 36% hydrochloric acid and activated carbon, and dissolved by heating. The solution was hot filtered. To the filtrate, 18 g of sodium chloride was added and dissolved. The solution thus obtained was gradually cooled to precipitate 3,3'-diamino-4,4'-difluorobenzophenone hydrochloride. The hydrochloride was filtered and neutralized in water with a 28% aqueous ammonia solution to obtain 82.3 g (83.0% yield) of 3,3'-diamino-4,4'-difluorobenzophenone. The purified product had purity of 99.1% by high performance liquid chromatography and a melting point of 130.8°–131.6° C.

|  | Elemental analysis | | | |
|---|---|---|---|---|
|  | C | H | N | F |
| Calculated (%) | 62.9 | 4.1 | 11.3 | 15.3 |
| Found (%) | 63.4 | 4.3 | 10.6 | 14.3 |

We claim:
1. A polyimide having recurring structural units of the formula (II):

wherein R is a tetravalent radical selected from the group consisting of an aliphatic radical having from 2 to 10 carbon atoms, alicyclic radical having from 4 to 10 carbon atoms, monoaromatic radical having the formula:

[benzene ring structure]

condensed polyaromatic radical having the formula:

[naphthalene structure]

and a noncondensed aromatic radical which is connected to each other with a direct bond or a bridge member and is represented by the formula:

[two benzene rings connected by X]

wherein X is a direct bond, —CO—, —O—, —S—, —SO$_2$—, —CH$_2$—, —C(CH$_3$)$_2$—, —C(CF$_3$)$_2$—, —O—[benzene]—O—

—C(=O)—[benzene]—C(=O)— or

—O—[benzene]—Y—[benzene]—O— wherein Y is a direct bond, —CO—, —O—, —S—, —SO$_2$—, —CH$_2$—, —C(CH$_3$)$_2$— or —C(CF$_3$)$_2$—, and n is an integer of 0 or 1.

2. A polyimide having recurring structural units of the formula (II):

$$\left( \text{structural formula} \right) \quad (II)$$

wherein R is a tetravalent radical selected from the group consisting of an aliphatic radical having from 2 to 10 carbon atoms, alicyclic radical having from 4 to 10 carbon atoms, monoaromatic radical having the formula:

[benzene ring structure]

condensed polyaromatic radical having the formula:

[naphthalene structure]

and a noncondensed aromatic radical which is connected to each other with a direct bond or a bridge member and is represented by the formula:

[two benzene rings connected by X]

wherein X is a direct bond, —CO—, —O—, —S—, —SO$_2$—, —CH$_2$—, —C(CH$_3$)$_2$—, —C(CF$_3$)$_2$—, —O—[benzene]—O—

—C(=O)—[benzene]—C(=O)— or

—O—[benzene]—Y—[benzene]—O— wherein Y is a direct bond, —CO—, —O—, —S—, —SO$_2$—, —CH$_2$—, —C(CH$_3$)$_2$— or —C(CF$_3$)$_2$—, and n is an integer of 0 or 1, and terminating the polymer chain with an aromatic radical which is substantially unsubstituted or substituted with a radical having no reactivity with amine or dicarboxylic anhydride.

3. The polyimide of claim 1 wherein the recurring structural units of the formula (II) is represented by the formula (II-A):

$$\left( \text{structural formula} \right) \quad (II-A)$$

wherein R is the same as above.

4. The polyimide of claim 2 wherein the recurring structural units of the formula (II) is represented by the formula (II-A):

wherein R is the same as above.

5. The polyimide of claim 1 wherein the recurring structural units of the formula (II) is represented by the formula (II-B):

wherein R is the same as above.

6. The polyimide of claim 2 wherein the recurring structural units of the formula (II) is represented by the formula (II-B):

wherein R is the same as above.

7. A process for preparing the polyimide of claim 1 by reacting an aromatic diamine primarily represented by the formula (I):

wherein n is an integer of 0 or 1, with a tetracarboxylic dianydride represented primarily by the formula (III):

wherein R is the same as above, and successively by thermally or chemically imidizing the resultant polyamic acid.

8. A process for preparing the polyimide of claim 2 by reacting an aromatic diamine primarily represented by the formula (I):

wherein n is an integer of 0 or 1, with a tetracarboxylic dianhydride primarily represented by the formula (III):

wherein R is the same as above, in the presence of an aromatic dicarboxylic anhydride selected from the group consisting of phthalic anhydride, 2,3-benzophenonedicarboxylic anhydride, 3,4-benzophenonedicarboxylic anhydride, 2,3-dicarboxyphenyl phenyl ether anhydride, 2,3-biphenyldicarboxylic anhydride, 3,4-biphenyldicarboxylic anhydride, 2,3-dicarboxyphenyl phenyl sulfone anhydride, 3,4-dicarboxyphenyl phenyl sulfone anhydride, 2,3-dicarboxyphenyl phenyl sulfide anhydride, 3,4-dicarboxyphenyl phenyl sulfide anhydride, 1,2-naphthalenedicarboxylic anhydride, 2,3-naphthalenedicarboxylic anhydride, 1,8-naphthalenedicarboxylic anhydride, 1,2-anthracenedicarboxylic anhydride, 2,3-anthracenedicarboxylic anhydride, 1,9-anthracenedicarboxylic anhydride and these dicarboxylic anhydride substituted with a radical having no reactivity with amine or dicarboxylic anhydride, and successively by thermally or chemically imidizing the resultant polyamic acid.

9. The process for preparing the polyimide of claim 8 wherein the aromatic diamine represented by the formula (I) is 3,3'-diamino-4,4'-difluorobenzophenone having the formula (I-A):

10. The process for preparing the polyimide of claim 8 wherein the aromatic diamine represented by the formula (I) is 1,3- or 1,4-bis(3-amino-4-fluorobenzoyl)-benzene having the formula (I-B):

11. A process for preparing the polyimide of claim 2 by reacting an aromatic diamine primarily represented by the formula (I):

wherein n is an integer of 0 or 1, with a tetracarboxylic acid dianhydride primarily represented by the formula (III):

wherein R is the same as above, in the presence of an aromatic monoamine selected from the group consisting of aniline, o-toluidine, m-toluidine, p-toluidine, 2,3-xylidine, 2,4-xylidine, 2,5-xylidine, 2,6-xylidine, 3,4-xylidine, 3,5-xylidine, o-chloroaniline, m-chloroaniline, p-chloroaniline, o-bromoaniline, m-bromoaniline, p-bromoaniline, o-nitroaniline, m-nitroaniline, p-nitroaniline, o-aminophenol, m-aminophenol, p-aminophenol, o-anisidine, m-anisidine, p-anisidine, o-phenetidine, m-phenetidine, p-phenetidine, o-aminobenzaldehyde, m-aminobenzaldehyde, p-aminobenzaldehyde, o-aminobenzonitrile, m-aminobenzonitrile, p-aminobenzonitrile, 2-aminobiphenyl, 3-aminobiphenyl, 4-aminobiphenyl, 2-aminophenyl phenyl ether, 3-aminophenyl phenyl ether, 4-aminophenyl phenyl ether, 2-aminobenzophenone, 3-aminobenzophenone, 4-aminobenzophenone, 2-aminophenyl phenyl sulfide, 3-aminophenyl phenyl sulfide, 4-aminophenyl phenyl sulfide, 2-aminophenyl phenyl sulfone, 3-aminophenyl phenyl sulfone, 4-aminophenyl phenyl sulfone, α-naphthylamine, β-naphthylamine, 1-amino-2-naphthol, 2-amino-1-naphthol, 4-amino-1-naphthol, 5-amino-1-napht hol, 5-amino-2-naphthol, 7-amino-2-naphthol, 8-amino-1-naphthol, 8-amino-7-naphthol, 8-amino-2-naphthol, 1-aminoanthracene, 2-aminoanthracene, 9-aminoanthracene and these aromatic monoamines having a radical having no reactivity with amine or dicarboxylic anhydride, and successively by thermally or chemically imidizing the resultant polyamic acid.

12. The process for preparing the polyimide of claim 11 wherein the aromatic diamine represented by the formula (I) is 3,3'-diamino-4,4'-difluorobenzophenone having the formula (I-A):

13. The process for preparing the polyimide of claim 11 wherein the aromatic diamine represented by the formula (I) is 1,3- or 1,4-bis(3-amino-4-fluorobenzoyl)-benzene having the formula (I-B):

14. The preparation process of the polyimide of claim 8 wherein the aromatic dicarboxylic anhydride is phthalic anhydride.

15. The preparation process of the polyimide of claim 11 wherein the aromatic monoamine is aniline.

16. The preparation process of the polyimide of claim 8 wherein the amount of the aromatic dicarboxylic anhydride is in the range of from 0.001 to 1.0 mole per mole of the aromatic diamine of the formula (I).

17. The preparation process of the polyimide of claim 14 wherein the amount of phthalic anhydride is in the range of from 0.001 to 1.0 mole per mole of the aromatic diamine of the formula (I).

18. The preparation process of the polyimide of claim 11 wherein the amount of the aromatic monoamine is the range of from 0.001 to 1.0 mole per mole of the tetracarboxylic dianhydride of the formula (II).

19. The preparation process of the polyimide of claim 15 wherein the amount of aniline is in the range of from 0.001 to 1.0 mole per mole of the tetracarboxylic dianhydride of the formula (II).

20. A composition comprising the polyimide of claim 2.

21. A composition comprising the polyimide of claim 1.

* * * * *